United States Patent [19]

Sköld

[11] Patent Number: 5,431,834
[45] Date of Patent: Jul. 11, 1995

[54] USE OF A TRIETHANOLAMINE PRODUCT MIXTURE

[75] Inventor: Rolf Sköld, Stenungsund, Sweden

[73] Assignee: Berol Nobel AB, Stenungsund, Sweden

[21] Appl. No.: 211,217

[22] PCT Filed: Oct. 7, 1992

[86] PCT No.: PCT/SE92/00701
§ 371 Date: Mar. 24, 1994
§ 102(e) Date: Mar. 24, 1994

[87] PCT Pub. No.: WO93/07241
PCT Pub. Date: Apr. 15, 1993

[30] Foreign Application Priority Data

Oct. 10, 1991 [SE] Sweden ............................ 9102931

[51] Int. Cl.$^6$ ................. C10M 133/08; C10M 173/00
[52] U.S. Cl. ............................. 252/51.5 R; 252/49.3; 252/77; 252/392
[58] Field of Search ................... 252/51.5 R, 49.3, 77, 252/392

[56] References Cited

U.S. PATENT DOCUMENTS 4,273,937  6/1981  Gum et al. .
4,420,414 12/1983  Valone .
4,726,914  2/1988  Fellows et al. .

FOREIGN PATENT DOCUMENTS 1140867  1/1969  United Kingdom .

Primary Examiner—Prince Willis, Jr.
Assistant Examiner—Cephia D. Toomer
Attorney, Agent, or Firm—Spencer, Frank & Schneider

[57] ABSTRACT

The process of providing functional fluids with at least one of corrosion inhibiting ability or defoaming properties, including adding to a functional fluid a triethanolamine product mixture containing a major part (at least 50%, preferably from 60–90%) by weight of at least one triethanolamine; a minor part (preferably from 10–40%) by weight of diethanolmono-$C_{3-4}$-alkanolamine and monoethanoldi-$C_{3-4}$-alkanolamine; and less than 1% by weight of a mixture of diethanolamine and monoethanolamine. Preferably the functional fluid is an aqueous metal working fluid.

8 Claims, No Drawings

USE OF A TRIETHANOLAMINE PRODUCT MIXTURE

This Application is a 371 of PCT/SE92/00701, Oct. 7, 1992.

BACKGROUND OF THE INVENTION

1. Field of the Invention

The present application relates to the use of a triethanolamine product mixture having a low content of diethanolamine and monoethanolamine in functional fluids, such as lubricants, metal working fluids and hydraulic fluids.

2. Description of the Related Art

The use of triethanolamine in a variety of industrial fluids is well known. Triethanolamines are normally produced in one or more steps by ethoxylating ammonia with ethylene oxide. In order to avoid the formation of polyalkyleneglycol chains, $HOC_2H_4(OC_2H_4)_n$, where $n>0$, and quaternization the nitrogen, atom the ethoxylation is normally stopped, when the reaction mixture contains 60–90% by weight of triethanolamine and 10–40% by weight of diethanolamine and monethanolamine. Such a reaction mixture may be subjected to distillation to obtain purer triethanolamine. The fact that the triethanolamine reaction product contains a large amount of diethanolamine has not previously been considered a real drawback, as diethanolamine contributes to anticorrosion properties, low foaming and desired alkalinity when used in functional fluids.

Recently, more attention has been paid to the fact the diethanolamine is toxic and forms nitrosamines, which are carcinogenic in animal tests. Therefore, a reduction of the content of diethanolamine is desirable. The content should, according to recommentations, be less than 1% by weight.

Thus, one object of the invention is to produce a triethanolamine product mixture which contains diethanolamine in an amount less than 1% by weight. This triethanolamine product mixture shall at least have about the same corrosion inhibiting ability and/or defoaming properties in functional fluids.

Another object of the invention is that the method of producing a triethanolamine product mixture shall be simple to perform and that the mixture shall be usable without any additional cleaning and/or working-up processes, such as distillation.

Still another object of the invention is to keep the formation of quaternized triethanolamine and polyalkylene glycol chain containing ethanolamine products to a low level.

SUMMARY OF THE INVENTION

According to the invention it has now been found that these objects can be met by using in functional fluids, a triethanolamine mixture containing a major part of triethanolamine, a minor part of diethanolmono-$C_{3-4}$-alkanolamine and monoethanoldi-$C_{3-4}$-alkanolamine, and less than 1% by weight of diethanolamine and monoethanolamine. By the expression "major part of triethanolamine" is here understood that said triethanolamine constitutes at least 50% by weight of the product mixture. The triethanol amine product mixture used in accordance with the invention can easily be obtained by reacting a conventional triethanolamine reaction mixture, obtained when reacting ammonia in one or more steps, with a $C_3$–$C_4$-alkylene oxide.

Such a process is described in British Patent No 1 140 867. Diethanolamine and monoethanolamine, which are both reactants in the process, have a catalytic effect and catalyze rather selectively their own alkoxylation. The presence of an effective amount of alkoxylation catalyst other than the diethanolamine and monoethanolamine shall preferably be avoided in order not to favour undesired side reactions. By the process, the contents of diethanolamine and monoethanolamine are reduced to less than 1% by weight, while the undesired side reactions, such as alkoxylation of hydroxyl groups or quarternization of the nitrogen atom is kept on a low level. In order to further suppress side reactions, it has been found suitable to perform the reaction below 160° C., preferably between 120°–150° C. The amount of alkylene oxide added has to be adjusted in relation to the amount of diethanolamine and monoethanolamine, so that the latter ones can be alkoxylated to the corresponding tertiary amine. Normally, the molar ratio of the alkylene oxide to the reactive hydrogen atoms bound to the nitrogen in diethanolamine and monoethanolamine is 1.0–1.4 and suitably 1.0–1.10.

The choice of alkylene oxide affects the HLB-value of the triethanolamine mixture formed during the reaction and the butylene oxide may be preferred if a product mixture with the more hydrophobic and surface active character is desired. Normally, the alkylene oxide used is propylene oxide. Both propylene oxide and butylene oxides react with a high selectivity with respect to the hydrogen atoms bound to the nitrogen atom in the primary and secondary amine resulting in a lower degree of side reactions like propoxylation of hydroxyl groups in monoethanolamine, diethanolamine or triethanolamine.

The triethanol amine product mixture used in accordance with the invention has many advantageous properties. Thus, application tests have clearly indicated that the triethanolamine product mixture is very suitable to replace triethanolamine as a component in aqueous functional fluids, such as lubricants, metal working fluids and hydraulic fluids. The diethanolmono-$C_3$–$C_4$-alkanolamine in the triethanolamine product mixture contributes to improved corrosion inhibiting and, low foaming properties.

DESCRIPTION OF THE PREFERRED EMBODIMENTS

The present invention is further illustrated by the following examples.

Example A 100 grams of a triethanolamine product mixture containing 85% by weight of triethanolamine and 15% by weight of diethanolamine and monoethanolamine (hereinafter referred to as TEA85) were reached with 8,4 grams of propylene oxide at 60° C. The ratio between the molecules of propylene oxide and the number of hydrogen atoms bound to a nitrogen atom was 1,01. After all propylene oxide had reacted the product obtained (hereinafter referred to as TEA85+PO) was analyzed with respect to the presence of secondary and primary ethanolamines. The total content of these alkanolamines was found to be less than 0,5% by weight.

Example B 100 grams of the same triethanolamine product mixture as specified in Example A were reacted with 10,4 grams of butylene oxide at 70° C. The ratio between the molecules of butylene oxide and the number of hydrogen atoms bound to a nitrogen atom was 1,00. After reaction with product mixture obtained (hereinafter referred to as TEA85-BO) was analyzed and the content of secondary and primary alkanolamines was found to be 0,7% by weight.

Example C 100 grams of the same triethanolamine products mixture as specified in Example A were reacted with 10.9 grams of propylene oxide at 150° C. The ratio between the molecules of propylene oxide and the number of hydrogen atoms bound to a nitrogen atom were 1.3. After reaction the content of secondary and primary alkanolamines was found to be less than 0.1% by weight.

EXAMPLE 1

The trietanolamine product mixtures TEA85-PO and TEA85-BO from Examples A and B were diluted with water having a water hardness of 0,2° dH to solutions containing 1, 2 and 3% by weight. The solutions were then neutralized with acetic acid to a pH-value of 9. As comparisons, corresponding solution were also formulated from the triethanolamine product mixture used as starting product in Example A (hereinafter referred to as TEA85) and a distillation product of TEA85 containing 99% by weight of triethanolamine. The latter product is hereinafter referred to as TEA99.

The twelve solutions were then tested with regard to their Fe corrosion according to cast iron chip-on-filter paper test (IP 287) and copper corrosion. In the measuring of copper corrosion, 0,2 grams of copper powder was mixed with 10 grams of glass beads in 200 ml of the solution containing the alkanolamines. The solutions were shaken for 24, 48 and 72 hours and the content of copper in the solutions was determined. The following results were obtained.

| Alkanolamine | Fe corrosion % of the filter paper stained Concentration | | |
|---|---|---|---|
| | 1% | 2% | 3% |
| TEA85 | 70 | 50 | 40 |
| TEA99 | 80 | 40 | 20 |
| TEA85-PO | 40 | 30 | 20 |
| TEA85-BO | 30 | 20 | 10 |

| Concentration | Cu corrosion Cu-content in the solution, ppm | | | | | | | | |
|---|---|---|---|---|---|---|---|---|---|
| | 1% | | | 2% | | | 3% | | |
| Time, h | 24 | 48 | 72 | 24 | 48 | 72 | 24 | 48 | 72 |
| TEA85 | 150 | 250 | 300 | 200 | 250 | 300 | 200 | 250 | 300 |
| TEA99 | 150 | 250 | 300 | 200 | 250 | 300 | 150 | 250 | 300 |
| TEA85-PO | 100 | 200 | 200 | 100 | 150 | 200 | 150 | 150 | 200 |
| TEA85-BO | 75 | 150 | 200 | 100 | 150 | 200 | 100 | 150 | 200 |

It is obvious that the alkanolamine product mixtures in accordance with the invention have favourable corrosion properties in comparison with prior used alkanolamine products.

EXAMPLE 2

The solutions of Example 1 containing 3% by weight of the alkanolamines were also tested with regard to foaming. 200 ml of each solution was vigorously stirred during 5 minutes and the volume of the fluid and the foam was measured. The following results were obtained.

| Alkanolamine | Volume[1] of foam and fluid ml Delay after stirring, min | | | |
|---|---|---|---|---|
| | 0 | 1 | 2 | 3 |
| TEA85 | 230 | 220 | 205 | 200 |
| TEA99 | 230 | 225 | 210 | 200 |
| TEA85-PO | 205 | 200 | | |
| TEA85-BO | 200 | | | |

[1]Volume of the solutions before stirring is 200 ml.

From the results it is evident that the product mixtures of the invention have a low foaming like the prior art products.

EXAMPLE 3

Synthetic metal working fluid concentrates were prepared from 20 parts by weight of TEA85-PO or TEA99, 25 parts by weight of dodecandioic acid, 55 parts by weight of distilled water and potassium hydroxide in an amount sufficient to give a pH of 9,8. The concentrates were then diluted with water having a water hardness of 200 ppm in accordance with the table below and tested with regard of foaming ability in accordance with Institute of Petroleum, IP 312 and with regard to iron corrosion in the same manner as in Example 1. The following results were obtained.

| Alkanol-amine | Dilution | Foaming | | Fe-corrosion % of filter paper stained |
|---|---|---|---|---|
| | | Initial foam heights, cm | Time to zero foam, s | |
| TEA99 | 1:20 | 20 | 15 | — |
| TEA85-PO | 1:20 | 20 | 8 | — |
| TEA99 | 1:70 | — | — | 5 |
| TEA85-PO | 1:70 | — | — | 3 |

From the results it is evident that the triethanolamine product mixture of the invention can advantageously replace TEA99.

What is claimed is:

1. The process of providing functional fluids with at least one of corrosion inhibiting ability or defoaming properties, comprising:
    adding to a functional fluid a triethanolamine product mixture comprised of:
    a major part by weight of triethanolamine;
    a minor part by weight of diethanolmono-$C_{3-4}$-alkanolamine and monoethanoldi-$C_{3-4}$-alkanolamine; and
    less than 1% by weight of a mixture of diethanolamine and monoethanolamine.

2. The process in accordance with claim 1, wherein the triethanolamine product mixture consists essentially of:
- a major part by weight of triethanolamine;
- a minor part by weight of diethanolmono-$C_{3-4}$-alkanolamine and monoethanoldi-$C_{3-4}$-alkanolamine; and
- less than 1% by weight of a mixture of diethanolamine and monoethanolamine.

3. The process in accordance with claim 2, wherein the functional fluid is an aqueous metal working fluid.

4. The process in accordance with claim 1, wherein the functional fluid is an aqueous metal working fluid.

5. The process of providing functional fluids with at least one of corrosion inhibiting ability or defoaming properties, comprising:
- adding to a functional fluid a triethanolamine product mixture comprised of:
  - from 60–90% by weight of triethanolamine;
  - from 10–40% by weight of a mixture of diethanolmono-$C_{3-4}$-alkanolamine and monoethanoldi-$C_{3-4}$-alkanolamine; and
  - less than 1% by weight of a mixture of diethanolamine and monoethanolamine.

6. The process in accordance with claim 5, wherein the triethanolamine product mixture consists essentially of:
- from 60–90% by weight of triethanolamine;
- from 10–40% by weight of a mixture of diethanolmono-$C_{3-4}$-alkanolamine and monoethanoldi-$C_{3-4}$-alkanolamine; and
- less than 1% by weight of a mixture of diethanolamine and monoethanolamine.

7. The process in accordance with claim 6, wherein the functional fluid is an aqueous metal working fluid.

8. The process in accordance with claim 5, wherein the functional fluid is an aqueous metal working fluid.

* * * * *